US012766218B2

(12) United States Patent
Yang et al.

(10) Patent No.: US 12,766,218 B2
(45) Date of Patent: Oct. 20, 2026

(54) HEMOSTATIC, ANTIBACTERIAL, AND HEALING-PROMOTING CLAY MINERAL-BASED BIOMATERIAL AND PREPARATION METHOD THEREOF

(71) Applicant: CHINA UNIVERSITY OF GEOSCIENCES (WUHAN), Wuhan (CN)

(72) Inventors: Huaming Yang, Wuhan (CN); Ying Chen, Wuhan (CN); Weimin Xie, Wuhan (CN); Yiting Yuan, Wuhan (CN)

(73) Assignee: CHINA UNIVERSITY OF GEOSCIENCES (WUHAN), Wuhan (CN)

( * ) Notice: Subject to any disclaimer, the term of this patent is extended or adjusted under 35 U.S.C. 154(b) by 232 days.

(21) Appl. No.: 18/415,669

(22) Filed: Jan. 18, 2024

(65) Prior Publication Data

US 2024/0307586 A1 Sep. 19, 2024

(30) Foreign Application Priority Data

Mar. 13, 2023 (CN) ........................ 202310247997.X

(51) Int. Cl.

*A61L 26/00* (2006.01)
*C08L 5/08* (2006.01)
*C08L 39/06* (2006.01)

(52) U.S. Cl.

CPC ......... *A61L 26/008* (2013.01); *A61L 26/0004* (2013.01); *A61L 26/0052* (2013.01); *C08L 5/08* (2013.01); *C08L 39/06* (2013.01); *A61L 2300/102* (2013.01); *A61L 2400/12* (2013.01); *A61L 2430/34* (2013.01)

(58) Field of Classification Search

CPC ............... A61L 26/008; A61L 26/0004; A61L 26/0052; A61L 2300/102; A61L 2400/12; A61L 2430/34; A61L 15/18; A61L 2300/404; A61L 2400/04; A61L 26/0066; A61L 26/0023; A61L 26/0061; A61L 2300/232; A61L 2300/412; C08L 5/08; C08L 39/06; Y02A 50/30

See application file for complete search history.

(56) References Cited

U.S. PATENT DOCUMENTS

| | | | | |
|---|---|---|---|---|
| 10,322,088 | B2 | 6/2019 | Sung et al. | |
| 11,033,655 | B1 | 6/2021 | Mccullen et al. | |
| 11,732,084 | B2 | 8/2023 | Mignon et al. | |
| 2007/0237811 | A1 * | 10/2007 | Scherr | A61L 26/0085 424/445 |
| 2016/0243163 | A1 * | 8/2016 | Mukherjee | A01N 25/28 |

FOREIGN PATENT DOCUMENTS

| | | | | | |
|---|---|---|---|---|---|
| CN | 107213508 | B | * | 4/2018 | A61K 35/02 |
| CN | 113563611 | A | * | 10/2021 | A61L 24/08 |
| KR | 20220100756 | A | * | 7/2022 | A61P 17/02 |

OTHER PUBLICATIONS

Biocompatible hydrogel (Year: 2021).*
Wound treatment and dressing (Year: 2022).*
An Iron containing oxide (Year: 2018).*

* cited by examiner

*Primary Examiner* — Snigdha Maewall

(57) ABSTRACT

A method for preparing for preparing the hemostatic, antibacterial, and healing-promoting clay mineral-based hydrogel in the present disclosure includes: dissolving chitosan uniformly in a dilute acid, adding a preset amount of a crosslinking agent to obtain a first mixture, and stirring the first mixture to allow complete dissolution; and adding a kaolinite@Prussian blue (PB) composite to obtain a second mixture, thoroughly stirring the second mixture, and drying a resulting system at room temperature to obtain the hemostatic, antibacterial, and healing-promoting clay mineral-based hydrogel, where the kaolinite@PB composite includes nano-kaolinite and PB in-situ growing on the nano-kaolinite. The present disclosure combines the kaolinite@PB composite with the chitosan, which can not only effectively overcome the defect that simple chitosan exhibits unsatisfactory antibacterial and healing-promoting effects, but also overcome the problem that a simple kaolinite@PB composite powder can hardly be used in practical applications.

9 Claims, 6 Drawing Sheets

HEMOSTATIC, ANTIBACTERIAL, AND HEALING-PROMOTING CLAY MINERAL-BASED BIOMATERIAL AND PREPARATION METHOD THEREOF

CROSS-REFERENCE TO RELATED APPLICATIONS

This application claims priority to Chinese Patent Application No. 202310247997.X with a filing date of Mar. 13, 2023. The content of the aforementioned application, including any intervening amendments thereto, is incorporated herein by reference.

TECHNICAL FIELD

The present disclosure relates to the technical field of biomedical materials, and in particular to a hemostatic, antibacterial, and healing-promoting clay mineral-based hydrogel and a preparation method thereof.

BACKGROUND

Uncontrolled bleeding is still a major cause of traumas and surgical death, and the use of a wound dressing as a hemostatic agent to control bleeding quickly and effectively is of great significance for wound healing. In order to prevent wound infection and provide an excellent wound healing microenvironment, a wound dressing should have a prominent antibacterial effect in addition to a rapid hemostatic effect. Although traditional wound dressings (such as gauzes and bandages) can play a role to some degree, most of the traditional wound dressings only have a single hemostatic function, exhibit poor biodegradability, and lack the functions of preventing bacterial infection and promoting tissue regeneration. A wound dressing with excellent degradability and antibacterial activity can also play a role of promoting wound recovery. Therefore, it is of significance to develop a wound dressing that not only exhibits a high mechanical strength, but also has hemostatic, anti-infection, and wound repair-promoting functions.

The novel wound dressings currently reported mainly include foams, films, sponges, and hydrogels. Hydrogels have attracted extensive attention due to their unique properties, for example, hydrogels can keep a wound environment moist, absorb excess exudate, allow oxygen permeation, cool a wound surface, and relieve the pain of a patient. As a natural polymer, chitosan is second only to cellulose in terms of reserves in the nature, and has excellent biocompatibility, hemostasis, antibacterial activity, and wound healing-promoting ability. As a result, chitosan has attracted great attention from researchers. However, a chitosan-based hydrogel alone has poor mechanical properties, unstable physical and chemical properties, and an unsatisfactory antibacterial effect, and is difficult to meet the actual use needs.

Although a hydrogel can serve as a physical barrier to protect a wound from bacterial infection, a hydrogel still needs to be used in combination with another antibacterial agent to exert an improved antibacterial effect, and the most common strategy is to introduce an antibacterial material into a hydrogel. However, the abuse of antibiotics leads to the emergence of drug-resistant bacteria, which may lead to treatment failure and poses a serious threat to human life and health. Therefore, there is an urgent need to develop a hydrogel dressing with intrinsic antibacterial activity.

SUMMARY OF PRESENT INVENTION

An objective of the present disclosure is to provide a hemostatic, antibacterial, and healing-promoting clay mineral-based hydrogel and a preparation method thereof in view of the above-mentioned deficiencies of the prior art.

The present disclosure provides a method for preparing a hemostatic, antibacterial, and healing-promoting clay mineral-based hydrogel, including the following steps: dissolving chitosan uniformly in a dilute acid to obtain a chitosan solution, adding a preset amount of a crosslinking agent to obtain a first mixture, and stirring the first mixture to allow complete dissolution; and adding a kaolinite@Prussian blue (PB) composite to obtain a second mixture, thoroughly stirring the second mixture, and drying a resulting system at room temperature to obtain the hemostatic, antibacterial, and healing-promoting clay mineral-based hydrogel, where the kaolinite@PB composite includes nano-kaolinite and PB in-situ growing on the nano-kaolinite.

In one embodiment, the nano-kaolinite is obtained through intercalation and stripping of pharmaceutical-grade kaolinite.

Further, a concentration of the kaolinite@PB composite in the chitosan solution is 0.5 mg/mL to 2 mg/mL.

In one embodiment, a method for preparing the nano-kaolinite includes: subjecting kaolinite to intercalation with dimethyl sulfoxide (DMSO) and urea successively, subjecting a resulting system to an ultrasonic treatment and centrifugation, and washing a resulting precipitate to obtain the nano-kaolinite.

In one embodiment, a mass percentage of the PB in the kaolinite@PB composite is 10% to 50%.

In one embodiment, the kaolinite@PB composite has a particle size of 200 nm to 500 nm.

Further, a mass percentage of the chitosan in the chitosan solution is 1% to 5%; a volume percentage of the dilute acid is 0.5% to 2%, and the dilute acid is one selected from the group consisting of an acetic acid and a hydrochloric acid; a mass of the crosslinking agent is 10% to 20% of a mass of the chitosan solution; the crosslinking agent is one or a combination of two or more selected from the group consisting of gelatin, glycerin, pectin, and polyvinyl alcohol (PVA); and the chitosan solution has a viscosity of higher than 400 Mpa·s.

In one embodiment, a method for preparing the kaolinite@PB composite includes the following steps: adding potassium ferricyanide and polyvinylpyrrolidone (PVP) to dilute hydrochloric acid, and subjecting a resulting mixture to stirring and an ultrasonic treatment at room temperature to obtain a homogeneous solution; and adding the nano-kaolinite to the homogeneous solution to obtain a mixed solution, subjecting the mixed solution to an ultrasonic treatment and thorough stirring, and allowing a resulting system to stand at a preset temperature to obtain the blue kaolinite@PB composite.

In one embodiment, the resulting system is allowed to stand for 15 h to 24 h in an oil/water bath at 60° C. to 90° C.; a mass ratio of the nano-kaolinite to the potassium ferricyanide is (1-4):3; and a mass ratio of the nano-kaolinite to the PVP is (1-4):60.

In one embodiment, a concentration of the dilute hydrochloric acid is 0.01 M to 0.1 M.

In one embodiment, the hydrogel obtained after the drying at room temperature is further sterilized under ultraviolet (UV) light.

The present disclosure also provides a hemostatic, antibacterial, and healing-promoting clay mineral-based hydrogel prepared by the preparation method described above.

In the kaolinite@PB composite used in the present disclosure, nano-kaolinite is adopted as a carrier, and PB in-situ grows and is loaded on a surface of the nano-kaolinite. The compounding of the nano-kaolinite and PB in a micro-nano form leads to a strong interfacial interaction, combines and enhances the hemostatic and antibacterial effects of the nano-kaolinite and PB, and allows an obvious synergistic enhancement effect. Thus, the kaolinite@PB composite of the present disclosure can not only accelerate the hemostasis, but also promote the wound healing. The PB has a photothermal effect, and the kaolinite has an adsorption effect for bacteria. The kaolinite can adsorb and aggregate increased bacteria to synergistically improve an antibacterial effect of the kaolinite@PB composite without obvious cytotoxicity and hemolysis. Thus, the kaolinite@PB composite has high biocompatibility and excellent safety, and can significantly enhance a hemostatic effect.

In the hemostatic, antibacterial, and healing-promoting clay mineral-based hydrogel prepared by the present disclosure, the kaolinite@PB composite with the above properties is added to significantly improve the antibacterial and hemostatic properties. In addition, the kaolinite@PB composite, the chitosan, and the crosslinking agent can form a crosslinked network structure through chemical and physical actions, which can greatly improve the mechanical properties of the clay mineral-based hydrogel.

The present disclosure combines the kaolinite@PB composite with the chitosan, which can not only effectively overcome the defect that simple chitosan exhibits unsatisfactory antibacterial and healing-promoting effects, but also overcome the problem that a simple kaolinite@PB composite powder can hardly be used in practical applications. The clay mineral-based hydrogel of the present disclosure does not cause a powder residue when in use, which is conducive to wound cleaning. The clay mineral-based hydrogel of the present disclosure can be easily used, and is especially suitable for hemostasis and healing of wounds in the field.

The hemostatic, antibacterial, and healing-promoting hydrogel prepared by the present disclosure has excellent mechanical properties due to various interactions such as hydrogen bonding, metal coordination, and electrostatic interaction.

The raw materials used in the present disclosure are widely-available and abundant, resulting in a low cost. The method for preparing the present disclosure involves simple steps and easy operations, and is conducive to large-scale production.

DETAILED DESCRIPTION OF THE EMBODIMENTS

Figure 1:
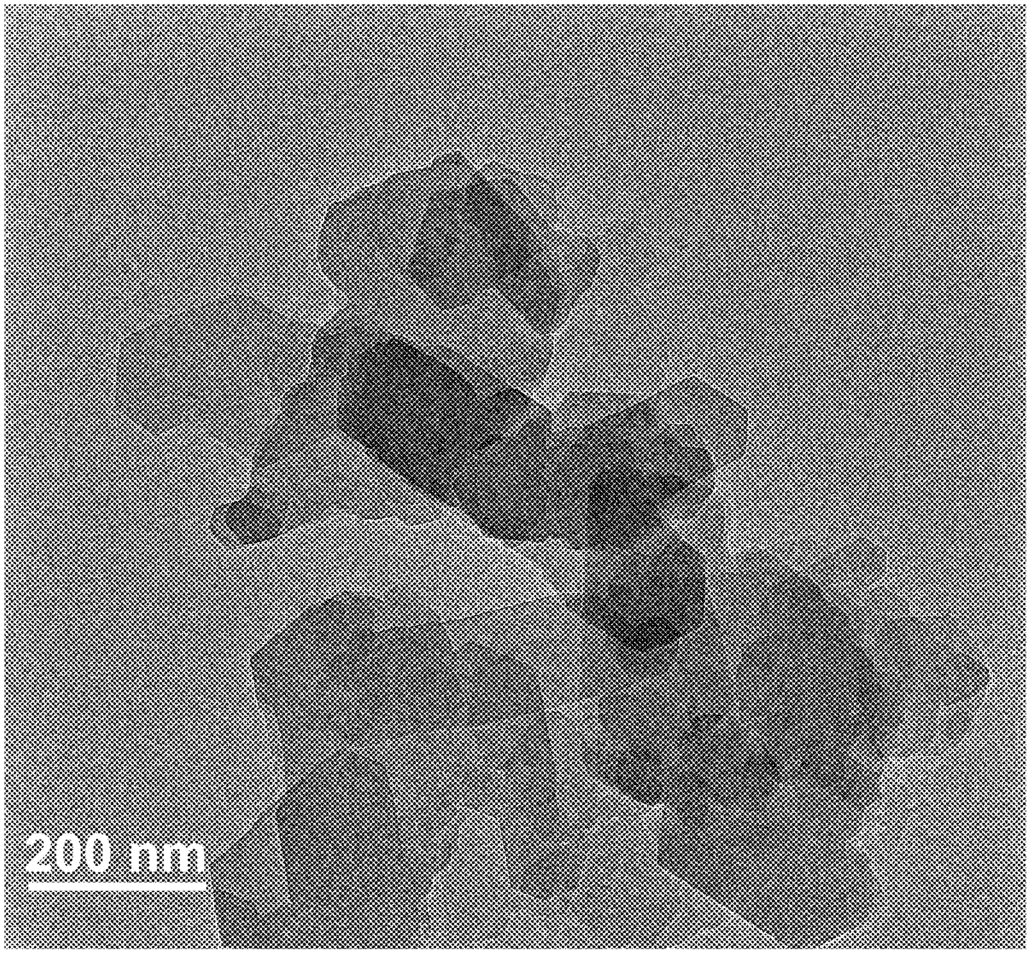
FIG. 1 shows a transmission electron microscopy (TEM) image of the nano-kaolinite (denoted as Kaol) prepared in Example 1.

The technical solutions of the present disclosure are described in further detail below with reference to the specific embodiments and accompanying drawings, but the present disclosure is not limited thereto.

The term "kaolinite" in this specification has a chemical formula of $Al_2O_3 \cdot 2SiO_2 \cdot 2H_2O$. In some forms, the kaolinite includes about 45.31% of silica, about 37.21% of alumina, and about 14.1% of water.

In this specification, the pharmaceutical-grade kaolinite in the examples is pharmaceutical-grade kaolinite from Shanghai Aladdin Biochemical Technology Co., Ltd., with a density of 2.53 g/cm$^3$.

A method for preparing the nano-kaolinite in the present disclosure includes the following steps:

(1) DMSO and deionized water are added in a volume ratio of (5-10):1 to a first reaction flask, 5% to 20% of kaolinite is weighed and added to the first reaction flask to obtain a first system, and the first system is stirred in an oil/water bath at 50° C. to 80° C. to allow a reaction for 20 h to 40 h to obtain a second system. The second system is centrifuged to obtain a first precipitate, and the first precipitate is washed with absolute ethanol and then dried for 24 h to obtain a first intercalation complex.

(2) A preset amount of urea is weighed and added to a second reaction flask, then 50 mL of deionized water is added to obtain a third system, and the third system is stirred for complete dissolution to obtain a saturated urea solution. The first intercalation complex is added to a third reaction flask, the saturated urea solution was added to obtain a fourth system, and the fourth system is stirred at room temperature to allow a reaction for 20 h to 48 h to obtain a fifth system. The fifth system is centrifuged to obtain a second precipitate, and the second precipitate is washed with absolute ethanol and then dried to obtain a second intercalation complex.

(3) The second intercalation complex is dispersed in deionized water, and a resulting dispersion is subjected to an ultrasonic treatment in a computer microwave/ultrasonic wave/UV combined catalysis synthesizer to allow a reaction for 2 h to obtain a sixth system. The sixth system is centrifuged to obtain a supernatant, and the supernatant is washed and then dried to obtain a kaolinite nanosheet.

Preparation of Nano-Kaolinite

Example 1

Nano-kaolinite was prepared by a step-by-step intercalation method, including the following steps: 90 mL of DMSO and 10 mL of deionized water were added to a first reaction flask, 10 g of pharmaceutical-grade kaolinite was added to the first reaction flask to obtain a first system, and the first system was stirred in a water bath at 60° C. to allow a reaction for 24 h to obtain a second system. The second system was centrifuged to obtain a first precipitate, and the first precipitate was washed three times with absolute ethanol and then dried at 60° C. for 24 h to obtain a first intercalation complex. 39 g of urea was weighed and added to a second reaction flask, 50 mL of deionized water was added to obtain a third system, and the third system was stirred for complete dissolution to obtain a 13 mol/L saturated urea solution. 5 g of the first intercalation complex was added to a third reaction flask, 50 mL of the saturated urea solution was added to obtain a fourth system, and the fourth system was stirred at a room temperature to allow a reaction for 48 h to obtain a fifth system. The fifth system was centrifuged at 8,000 rpm to obtain a second precipitate, and the second precipitate was washed three times with absolute ethanol and then dried at 60° C. overnight to obtain a second intercalation complex. 2 g of the second intercalation complex was dispersed in 200 mL of deionized water, and a resulting dispersion was subjected to an ultrasonic treatment for 2 h at 100° C. and 1,000 W in a computer microwave/ultrasonic wave/UV combined catalysis synthesizer to allow a reaction to obtain a sixth system. The sixth system was centrifuged at 4,000 rpm to obtain a supernatant, and the supernatant was washed three times and then lyophilized under vacuum to obtain the nano-kaolinite, which was denoted as Kaol.

FIG. 1 is a TEM image of the nano-kaolinite (denoted as Kaol) prepared in Example 1, which reflects a nanostructure of kaolinite.

Preparation of Kaolinite@PB Composites

Example 2

Figure 2:
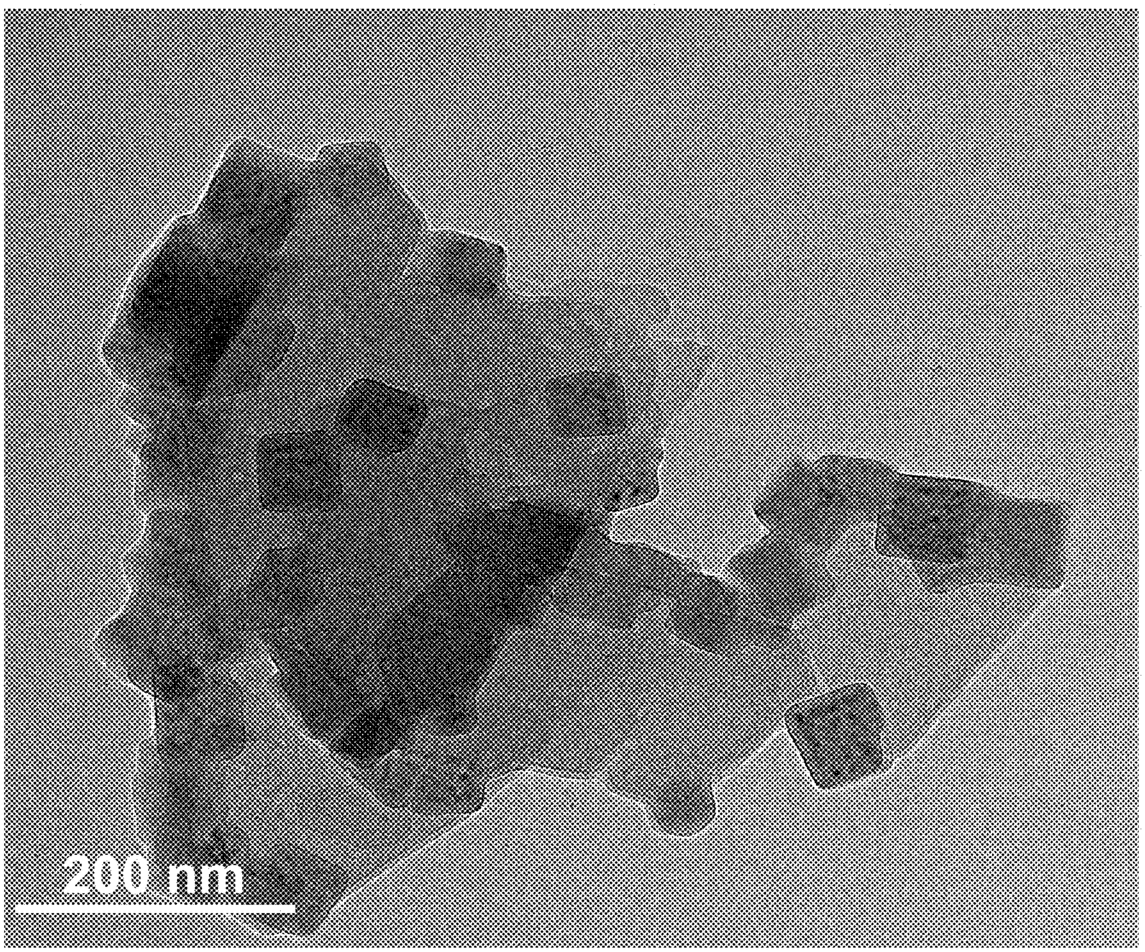
FIG. 2 shows a TEM image of the kaolinite@PB composite (denoted as Kaol@PB-1) prepared in Example 2.

In this example, a method for preparing a kaolinite@PB composite was provided, including the following steps: 3 g of PVP was weighed and added to a 100 mL flask, then 40 mL of a 0.01 M dilute hydrochloric acid was added to obtain a first mixture, and the first mixture was ultrasonically treated and stirred until the PVP was completely dissolved. 100 mg of nano-kaolinite was added to obtain a second mixture, and the second mixture was ultrasonically treated and stirred to allow complete dissolution. Then 131.7 mg of potassium ferricyanide was added to obtain a third mixture, and the third mixture was ultrasonically treated and stirred. A resulting system was allowed to stand in an oil bath heated to 80° C. to allow a reaction for 24 h, and then centrifuged, and a resulting supernatant was washed and lyophilized to obtain the kaolinite@PB composite, which was denoted as Kaol@PB-1. FIG. 2 is a TEM image of Kaol@PB-1.

Example 3

In this example, a method for preparing a kaolinite@PB composite was provided, including the following steps: 3 g of PVP was weighed and added to a 100 mL flask, then 40 mL of a 0.01 M dilute hydrochloric acid was added to obtain a first mixture, and the first mixture was ultrasonically treated and stirred until the PVP was completely dissolved. 50 mg of nano-kaolinite was added to obtain a second mixture, and the second mixture was ultrasonically treated and stirred to allow complete dissolution. Then 131.7 mg of potassium ferricyanide was added to obtain a third mixture, and the third mixture was ultrasonically treated and stirred. A resulting system was allowed to stand in an oil bath heated to 80° C. to allow a reaction for 24 h, and then centrifuged, and a resulting supernatant was washed and lyophilized to obtain the kaolinite@PB composite, which was denoted as Kaol@PB-2.

Example 4

In this example, a method for preparing a kaolinite@PB composite was provided, including the following steps: 3 g of PVP was weighed and added to a 100 mL flask, then 40 mL of a 0.01 M dilute hydrochloric acid was added to obtain a first mixture, and the first mixture was ultrasonically treated and stirred until the PVP was completely dissolved. 200 mg of nano-kaolinite was added to obtain a second mixture, and the second mixture was ultrasonically treated and stirred to allow complete dissolution. Then 131.7 mg of potassium ferricyanide was added to obtain a third mixture, and the third mixture was ultrasonically treated and stirred. A resulting system was allowed to stand in an oil bath heated to 80° C. to allow a reaction for 24 h, and then centrifuged, and a resulting supernatant was washed and lyophilized to obtain the kaolinite@PB composite, which was denoted as Kaol@PB-3.

Preparation of Hemostatic, Antibacterial, and Healing-Promoting Clay Mineral-Based Hydrogels

Example 5

Figure 4:
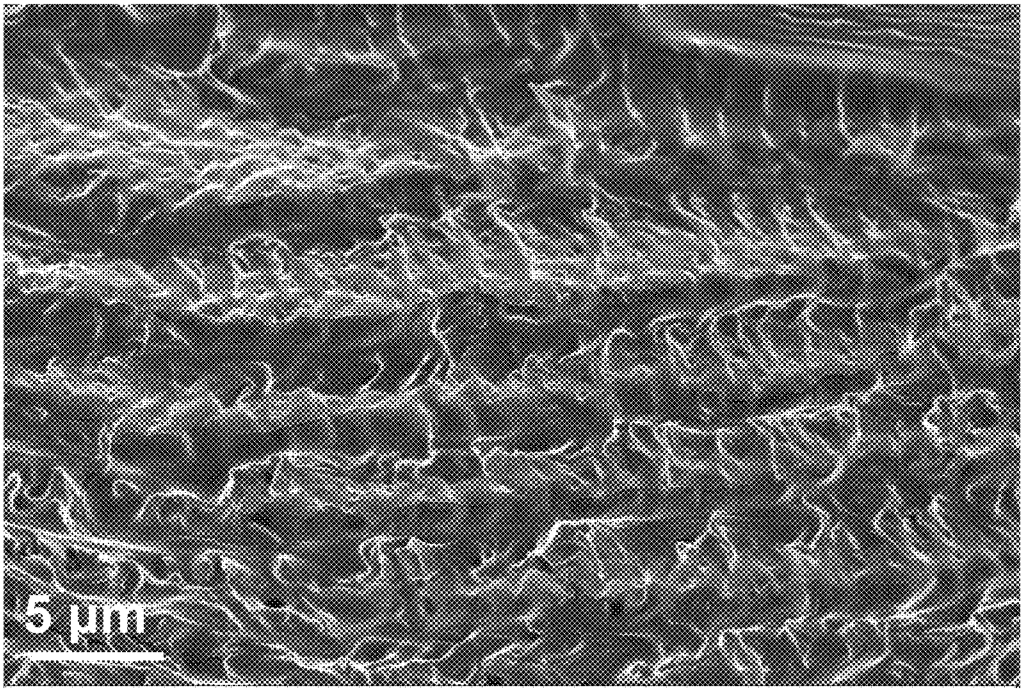
FIG. 4 shows a scanning electron microscopy (SEM) image of the hemostatic, antibacterial, and healing-promoting clay mineral-based hydrogel (denoted as Kaol@PB/Chit) prepared in Example 5.

2 g of high-viscosity (larger than 400 Mpa·s) chitosan was added to 50 mL of an acetic acid with a volume percentage of 1% to obtain a first mixture, and the first mixture was stirred in a water bath at 50° C. until the chitosan was completely dissolved. Then 3 g of gelatin was added to obtain a second mixture, and the second mixture was stirred until the gelatin was completely dissolved. 12 g of glycerin was added to obtain a third mixture, and the third mixture was stirred for 2 h. Kaol@PB-1 was added at a final concentration of 1 mg/mL to obtain a fourth mixture, and the fourth mixture was thoroughly stirred, then placed with a thickness of about 8 mm in a mold, and dried at room temperature for 2 d. A resulting product was cut with scissors, which was denoted as Kaol@PB/Chit. FIG. 4 is an SEM image of Kaol@PB/Chit, and it can be seen that a crosslinked network structure is formed.

Example 6

2 g of high-viscosity (larger than 400 Mpa·s) chitosan was added to 50 mL of an acetic acid with a volume percentage of 1% to obtain a first mixture, and the first mixture was stirred in a water bath at 50° C. until the chitosan was completely dissolved. Then 3 g of gelatin was added to obtain a second mixture, and the second mixture was stirred until the gelatin was completely dissolved. 12 g of glycerin was added to obtain a third mixture, and the third mixture was stirred for 2 h. Kaol@PB-2 was added at a final concentration of 1 mg/mL to obtain a fourth mixture, and the fourth mixture was thoroughly stirred and then placed with a thickness of about 8 mm in a mold.

Example 7

2 g of high-viscosity (larger than 400 Mpa·s) chitosan was added to 50 mL of an acetic acid with a volume percentage of 1% to obtain a first mixture, and the first mixture was stirred in a water bath at 50° C. until the chitosan was completely dissolved. Then 3 g of gelatin was added to obtain a second mixture, and the second mixture was stirred until the gelatin was completely dissolved. 12 g of glycerin was added to obtain a third mixture, and the third mixture was stirred for 2 h. Kaol@PB-3 was added at a final concentration of 1 mg/mL to obtain a fourth mixture, and the fourth mixture was thoroughly stirred and then placed with a thickness of about 8 mm in a mold.

Example 8

This example was different from Example 5 in that an amount of acetic acid was increased:

2 g of high-viscosity (larger than 400 Mpa·s) chitosan was added to 50 mL of an acetic acid with a volume percentage of 2% to obtain a first mixture, and the first mixture was stirred in a water bath at 50° C. until the chitosan was completely dissolved. Then 3 g of gelatin was added to obtain a second mixture, and the second mixture was stirred until the gelatin was completely dissolved. 12 g of glycerin was added to obtain a third mixture, and the third mixture was stirred for 2 h. Kaol@PB-1 was added at a final concentration of 1 mg/mL to obtain a fourth mixture, and the fourth mixture was thoroughly stirred and then placed with a thickness of about 8 mm in a mold.

Example 9

This example was different from Example 5 in that an amount of the kaolinite@PB composite (Kaol@PB-1) was increased:

2 g of high-viscosity (larger than 400 Mpa·s) chitosan was added to 50 mL of an acetic acid with a volume percentage of 1% to obtain a first mixture, and the first mixture was stirred in a water bath at 50° C. until the chitosan was completely dissolved. Then 3 g of gelatin was added to obtain a second mixture, and the second mixture was stirred until the gelatin was completely dissolved. 12 g of glycerin was added to obtain a third mixture, and the third mixture was stirred for 2 h. Kaol@PB-1 was added at a final concentration of 1 mg/mL to obtain a fourth mixture, and the fourth mixture was thoroughly stirred and then placed with a thickness of about 8 mm in a mold.

Example 10

This example was different from Example 5 in that an amount of the glycerin was reduced:

2 g of high-viscosity (larger than 400 Mpa·s) chitosan was added to 50 mL of an acetic acid with a volume percentage of 1% to obtain a first mixture, and the first mixture was stirred in a water bath at 50° C. until the chitosan was completely dissolved. Then 3 g of gelatin was added to obtain a second mixture, and the second mixture was stirred until the gelatin was completely dissolved. 5 g of glycerin was added to obtain a third mixture, and the third mixture was stirred for 2 h. Kaol@PB-1 was added at a final concentration of 1 mg/mL to obtain a fourth mixture, and the fourth mixture was thoroughly stirred and then placed with a thickness of about 8 mm in a mold.

Comparative Example 1

This comparative example was different from Example 5 in that the kaolinite@PB composite (Kaol@PB-1) was not added:

2 g of high-viscosity (larger than 400 Mpa·s) chitosan was added to 50 mL of an acetic acid with a volume percentage of 1% to obtain a first mixture, and the first mixture was stirred in a water bath at 50° C. until the chitosan was completely dissolved. Then 3 g of gelatin was added to obtain a second mixture, and the second mixture was stirred until the gelatin was completely dissolved. 12 g of glycerin was added to obtain a third mixture, and the third mixture was stirred for 2 h, then placed with a thickness of about 8 mm in a mold, and dried at room temperature for 2 d. a resulting product was cut with scissors, which was denoted as Chit.

Comparative Example 2

This comparative example was different from Example 5 in that the kaolinite@PB composite (Kaol@PB-1) was replaced with nano-kaolinite (Kaol):

2 g of high-viscosity (larger than 400 Mpa·s) chitosan was added to 50 mL of an acetic acid with a volume percentage of 1% to obtain a first mixture, and the first mixture was stirred in a water bath at 50° C. until the chitosan was completely dissolved. Then 3 g of gelatin was added to obtain a second mixture, and the second mixture was stirred until the gelatin was completely dissolved. 12 g of glycerin was added to obtain a third mixture, and the third mixture was stirred for 2 h. Kaol was added at a final concentration of 1 mg/mL to obtain a fourth mixture, and the fourth mixture was thoroughly stirred, then placed with a thickness of about 8 mm in a mold, and dried at room temperature for 2 d; and a resulting product was cut with scissors, which was denoted as Kaol/Chit.

Performance Analysis

1. Study on Properties of Kaolinite@PB Composites

Figure 3:
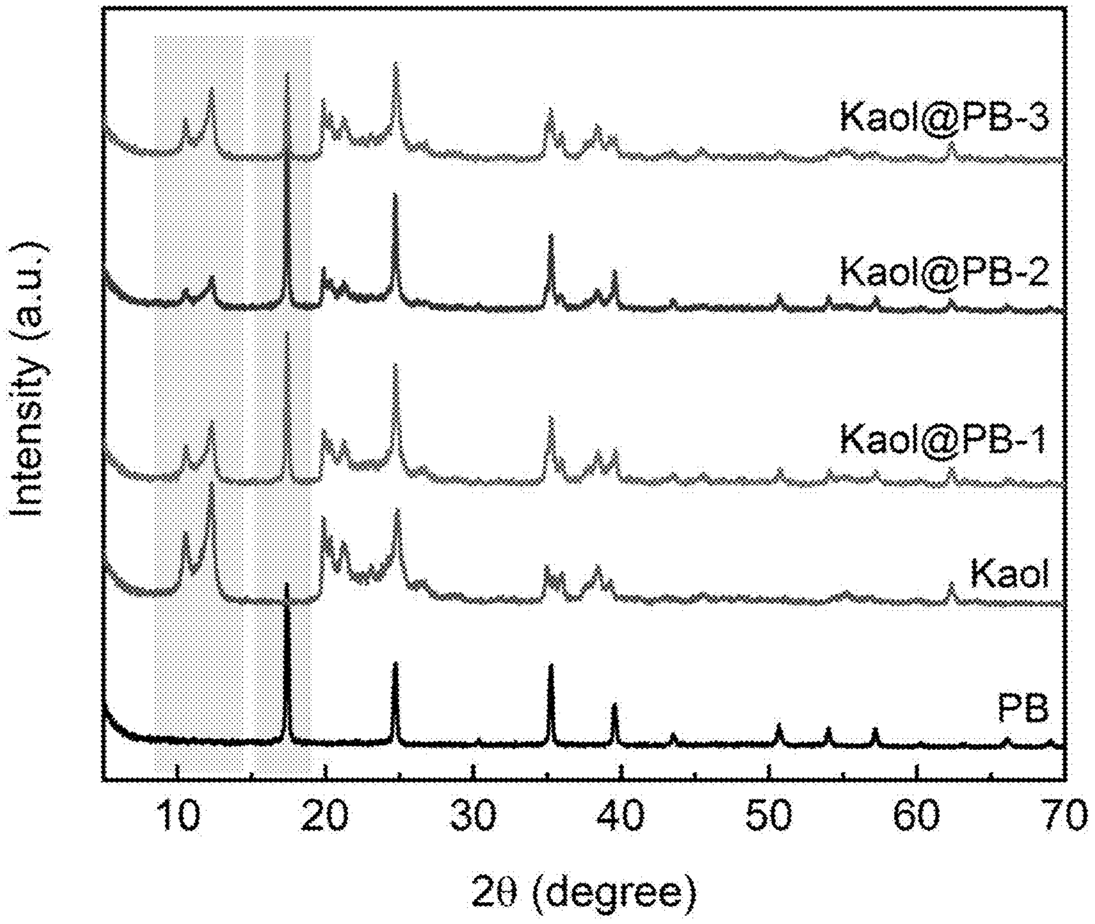
FIG. 3 shows X-ray diffraction (XRD) patterns of the kaolinite@PB composites prepared in the present disclosure.

Identification of kaolinite@PB composites: The kaolinite@PB composites each were identified by the XRD technology. As shown in FIG. 3, the samples prepared in Examples 2, 3, and 4 have obvious characteristic diffraction peaks of kaolinite and PB, indicating the successful preparation of the kaolinite@PB composites. As shown in FIG. 2, PB of a cube structure grows uniformly on flaky kaolinite.

Antibacterial experiment: A colony-counting method was adopted. Single colonies of *Staphylococcus aureus* (*S. aureus*) (ATCC 25923) were picked and streaked on a first plate and cultivated in a shaker at 37° C. for 6 h, and a resulting bacterial solution was diluted $1\times10^4$ times. An antibacterial powder was added at concentrations of 100 μg/mL, 200 μg/mL, 300 μg/mL, and 400 μg/mL, and a resulting mixture was irradiated with 808 nm near-infrared (NIR) light (power: 1 W) for 6 min, then diluted 10 times, coated on a second plate, and cultivated for 12 h. The second plate was photographed, and a number of colonies on the second plate was recorded. Antibacterial results of each sample were shown in Table 1.

TABLE 1

Antibacterial results

| Concentration (μg/mL) | Bacterial survival rate (%) | | | | | | | |
|---|---|---|---|---|---|---|---|---|
| | Kaol | Kaol + L | Kaol@PB-1 | Kaol@PB-1 + L | Kaol@PB-2 | Kaol@PB-2 + L | Kaol@PB-3 | Kaol@PB-3 + L |
| 100 | 91 ± 1 | 85 ± 1 | 95 ± 10 | 83 ± 2 | 92 ± 10 | 70 ± 11 | 133 ± 2 | 117 ± 7 |
| 200 | 101 ± 6 | 93 ± 4 | 90 ± 6 | 79 ± 1 | 80 ± 8 | 0.0 | 113 ± 7 | 74 ± 9 |
| 300 | 91 ± 6 | 84 ± 3 | 86 ± 12 | 0.0 | 69 ± 6 | 0.0 | 102 ± 9 | 46 ± 5 |
| 400 | 97 ± 6 | 83 ± 5 | 75 ± 13 | 0.0 | 69 ± 3 | 0.0 | 94 ± 12 | 1 ± 0 |

It can be seen from Table 1 that the Kaol@PB composites with antibacterial functions prepared in Examples 2, 3, and 4 exhibit excellent inhibitory effects for *S. aureus*. It fully indicates that the Kaol@PB composite prepared by the present disclosure has an excellent antibacterial effect.

In vivo hemostasis experiment: 8-10 week-old Balb-C male mice each with a body weight of 22 g to 24 g were selected. The mice each were anesthetized and subjected to abdominal incision to expose a liver; a tissue fluid around the liver was carefully removed, and a filter paper pre-weighed was placed underneath the liver; a 1 cm-long wound was formed by a scalpel on the liver, and after bleeding, a sample was applied to fully cover the wound, during which a bleeding site was slightly pressed; and a bleeding time was recorded by a stopwatch. A criterion for hemostasis was that no blood was ejected or oozed from the wound, that is, blood was coagulated. A group that did not receive any treatment was adopted as a control group. A hemostasis time of each sample was shown in Table 2.

TABLE 2

| Hemostasis time | | | |
|---|---|---|---|
| Sample | Material | Bleeding time (s) | Bleeding amount (g) |
| Blank control group | No material | 249 ± 20 | 0.27 ± 0.039 |
| Example 1 | Kaol | 104 ± 6 | 0.12 ± 0.012 |
| Example 2 | Kaol@PB-1 | 83 ± 12 | 0.070 ± 0.026 |
| Example 3 | Kaol@PB-2 | 57 ± 10 | 0.058 ± 0.022 |
| Example 4 | Kaol@PB-3 | 74 ± 9 | 0.08 ± 0.031 |

It can be seen from Table 2 that the loading of PB on a surface of kaolinite can effectively improve a hemostatic effect of the kaolinite.

Cytotoxicity Test:

Cytotoxicities of composites: Human skin fibroblasts BJ were used to evaluate the biocompatibility of each composite. The human skin fibroblasts were cultivated with a 1640 medium including 10% of fetal bovine serum (FBS) and 1% of penicillin-streptomycin. The BJ cells were cultivated in a sterile environment with 5% $CO_2$ at 37° C. The original medium was replaced with a fresh medium every two days until the cells reached an appropriate degree of aggregation.

Assessment of cytotoxicity by a CCK8 method: 100 μL of a cell suspension with a concentration of $1\times10^4$ cells/mL was inoculated to each well of a 96-well plate and cultivated for 12 h. Then 100 μL of a material solution with a concentration of 100 μg/mL was added to each well, and the plate was incubated for 24 h; the original medium was removed, and 100 μL of a CCK8 solution was added to each well. Then the cells were further cultivated for 1 h, and the absorbance was measured with a microplate reader (450 nm). Three parallel experiments were set. A group in which no material was added was adopted as a blank control group.

It can be seen from assessment results of cytotoxicity of each material for fibroblasts that the nano-kaolinite prepared in Example 1 and the kaolinite@PB composites prepared in Examples 2, 3, and 4 exhibit almost no obvious toxicity for fibroblasts, and have excellent biocompatibility.

Hemolysis experiment: 900 μL of a 1 mg/mL composite solution was thoroughly mixed with 100 μL of a 10% red blood cell (RBC) solution, a resulting mixed solution was incubated in a 37° C. water bath for 1 h and then centrifuged at 3,000 rpm for 5 min, a resulting supernatant was collected, and an absorbance value of the supernatant at 540 nm was determined by a microplate reader. Deionized water and phosphate-buffered saline (PBS) were adopted as positive and negative control groups, respectively.

$$\text{Hemolysis rate (\%)} = (OD_{sample} - OD_{negative})/(OD_{positive} - OD_{negative}) \times 100\%.$$

The nano-kaolinite prepared in Example 1 has a hemolysis rate of 30%, indicating hemolysis. The kaolinite@PB composites prepared in Examples 2, 3, and 4 have a hemolysis rate of lower than 5%, indicating slight hemolysis.

2. Study on Hemostatic, Antibacterial, and Healing-Promoting Properties of Hydrogels Hemolysis experiment: A composite hydrogel with a diameter of 2 cm was mixed with 100 μL of a 10% RBC solution (blood from an ear vein of a New Zealand white rabbit), and a resulting mixed solution was incubated at 37° C. for 10 min. Then 5 mL of deionized water was added dropwise, during which a blood clot was prevented from being broken; 4 mL of a liquid was collected and centrifuged at 1,000 rpm for 1 min; a resulting supernatant was collected and incubated in a 37° C. water bath for 1 h, and then 200 μL of the supernatant was taken and transferred to a 96-well plate. The absorbance of the supernatant at 540 nm was measured by a microplate reader. 3 replicates were set for each sample. Deionized water and PBS were adopted as positive and negative control groups, respectively.

$$\text{Hemolysis rate (\%)} = (OD_{sample} - OD_{negative})/(OD_{positive} - OD_{negative}) \times 100\%.$$

In vitro hemostasis experiment: A composite hydrogel with a diameter of 2 cm was mixed with 100 μL of anticoagulant rabbit blood (blood from an ear vein of a New Zealand white rabbit), then 10 μL of a 0.2 M $CaCl_2$ solution was immediately added to trigger coagulation, and a resulting system was incubated at 37° C. for 10 min. Then 5 mL of deionized water was added dropwise, during which a blood clot was prevented from being broken. 4 mL of a liquid was collected and centrifuged at 1,000 rpm for 1 min. A resulting supernatant was collected and incubated in a 37° C. water bath for 1 h, and then 200 μL of the supernatant was taken and transferred to a 96-well plate. The absorbance of the supernatant at 540 nm was measured by a microplate reader. A group in which no sample was added was adopted as a blank control group. 3 replicates were set for each sample.

The composite hydrogels prepared in Example 5, Comparative Example 1, and Comparative Example 2 all have a low hemolysis rate of lower than 5%, indicating negligible hemolysis. The composite hydrogels all have an excellent in vitro hemostatic effect.

Antibacterial experiment: A plate count method was used to detect antibacterial activities of the hydrogels prepared in Example 5, Comparative Example 1, and Comparative Example 2. *Escherichia coli* (*E. coli*) (ATCC 25922) and *S. aureus* (ATCC 25923) were used for determination of an antibacterial activity. Single colonies were picked and streaked on a plate, cultivated in a shaker at 37° C. for 4 h, and diluted $1\times10^4$ times; a prepared hydrogel was added, and a resulting mixture was irradiated with 808 nm NIR light (power: 1 W) for 6 min and then cultivated in an incubator for 1 h; 50 μL of a resulting bacterial solution was evenly spread on an LB agar plate and incubated at 37° C. for 12 h under shaking. The LB agar plate was photographed, and a number of colonies on the LB agar plate was recorded. Antibacterial results of each sample were shown in Table 3.

TABLE 3

Antibacterial results

| Sample | Material | Whether there is light | Bacterial survival rate (%) *E. coli* | *S. aureus* |
|---|---|---|---|---|
| Blank | No material | −L | 100 ± 2 | 100 ± 1 |
| | | +L | 94 ± 3 | 92 ± 4 |
| Comparative Example 1 | Chit | −L | 67 ± 3 | 69 ± 1 |
| | | +L | 64 ± 5 | 68 ± 2 |
| Comparative Example 2 | Kaol/Chit | −L | 80 ± 6 | 83 ± 1 |
| | | +L | 80 ± 3 | 86 ± 2 |
| Example 5 | Kaol@PB/Chit | −L | 80 ± 3 | 84 ± 3 |
| | | +L | 0 | 0 |

It can be seen from the data in Table 3 that the Kaol@PB/Chit hydrogel with an antibacterial function prepared in Example 5 exhibits excellent inhibitory effects for *E. coli* and *S. aureus*. It fully indicates that the hemostatic, antibacterial, and healing-promoting hydrogel of the present disclosure has an excellent antibacterial effect.

Wound healing experiment: Male Balb-C mice each with a body weight of 22 g to 24 g were selected and randomly grouped according to body weights. Each mouse in each group was intraperitoneally injected with chloral hydrate (5%) for anaesthetization, and a circular wound with a size of 0.8 cm×0.8 cm was cut by scissors on the dorsal skin of the mouse; and 50 μL of a mixed bacterial solution of *E. coli* (ATCC 25922) and *S. aureus* (ATCC 25923) (a concentration of each strain was $1\times10^9$ CFU mL-1) was dropped to allow infection for 1 d, and then the hydrogels prepared in Example 5, Comparative Example 1, and Comparative Example 2 each were applied and then irradiated with 808 nm NIR light (1 W) for 6 min (+L). A group in which no material was applied was adopted as a blank control group, and groups in which the hydrogels prepared in Example 5, Comparative Example 1, and Comparative Example 2 were applied but not irradiated with light (−L) were adopted as negative control groups. A wound area of each mouse in each group was measured on day 0, day 10, and day 14; and bacteria were collected from each wound for bacterial concentration detection on day 7. Antibacterial and healing-promoting data were shown in Table 4. Antibacterial effects were shown in FIG. 5.

TABLE 4

Antibacterial effects

| Sample | Material | Whether there is light | 7 d bacterial count at a wound | Proportion of a relative 14 d wound area (%) |
|---|---|---|---|---|
| Blank | No material | − | 2225 | 17.91 ± 4.80 |
| | | + | 2029 | 15.49 ± 1.90 |
| Example 5 | Kaol@PB/Chit | − | 2238 | 13.80 ± 1.88 |
| | | + | 160 | 11.01 ± 1.83 |
| Comparative Example 1 | Chit | − | 2375 | 14.71 ± 2.23 |
| | | + | 1980 | 15.14 ± 7.47 |
| Comparative Example 2 | Kaol/Chit | − | 2940 | 16.75 ± 1.60 |
| | | + | 2108 | 18.62 ± 2.01 |

Figure 5:
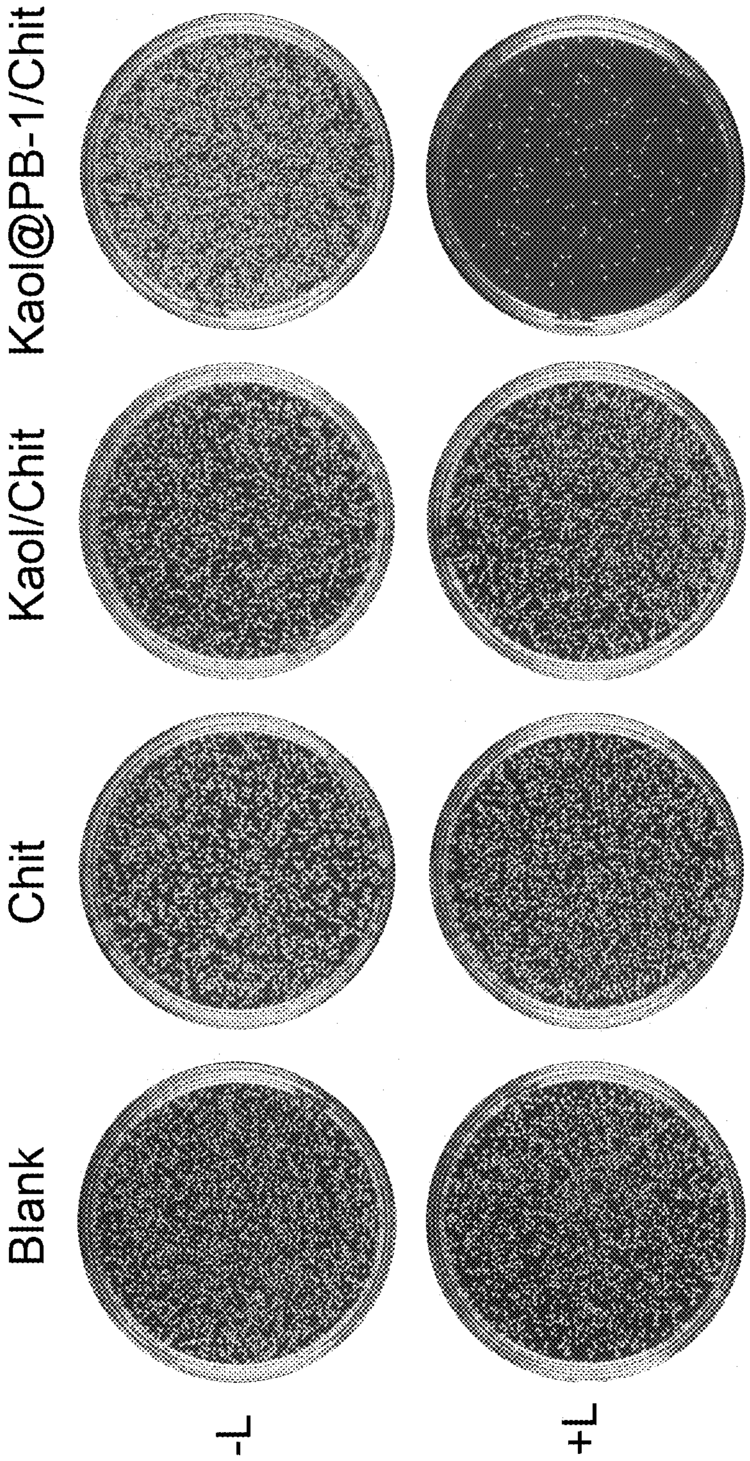
FIG. 5 shows a picture of wound-derived bacteria-coated plates of Example 5, Comparative Example 1, and Comparative Example 2 on day 7 in a wound healing experiment.

It can be seen from the data in Table 4 and FIG. 5 that the hemostatic, antibacterial, and healing-promoting hydrogel prepared in Example 5 can effectively inhibit the proliferation of bacteria at a wound and significantly promote the healing of a wound, indicating significant antibacterial and healing-promoting effects.

Mechanical property test of materials: The prepared hydrogel materials each were cut to a size of 8 mm×30 mm and then subjected to a tensile property test. Experimental results were shown in FIG. 6.

Figure 6:
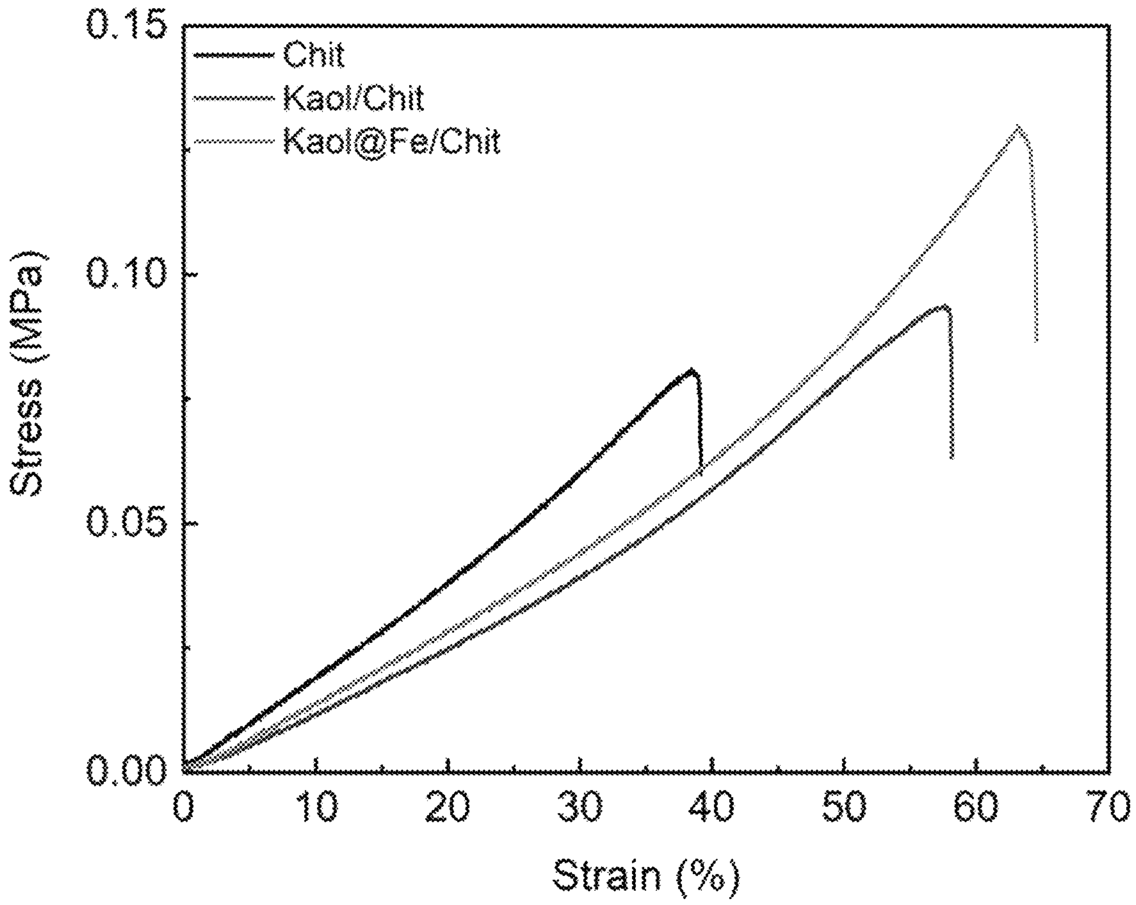
FIG. 6 shows stress-strain curves of Example 5, Comparative Example 1, and Comparative Example 2.

It can be seen from FIG. 6 that the addition of the kaolinite@PB composite can improve the mechanical properties of the hydrogel, which is related to physical and chemical interactions among the raw materials of the present application, such as coordination of iron ions in PB with hydroxyl on a surface of kaolinite and hydroxyl in chitosan. As a result, a hydrogel composite with a double-crosslinked structure is produced in the present disclosure.

What is not mentioned above can be acquired in the prior art.

Although some specific embodiments of the present disclosure have been described in detail by way of examples, those skilled in the art will appreciate that the above examples are provided for illustration only and not for limiting the scope of the present disclosure. A person skilled in the art can make various modifications or supplements to the specific embodiments described or replace them in a similar manner, but it may not depart from the direction of the present disclosure or the scope defined by the appended claims. Those skilled in the art should understand that any modification, equivalent replacement, and improvement that are made to the above embodiments according to the technical essence of the present disclosure shall be included in the protection scope of the present disclosure.

What is claimed is:

1. A method for preparing a hemostatic, antibacterial, and healing-promoting clay mineral-based hydrogel, comprising the following steps:

dissolving chitosan uniformly in a dilute acid to obtain a chitosan solution, adding a preset amount of a cross-linking agent to obtain a first mixture, and stirring the first mixture to allow complete dissolution; and adding a kaolinite and Prussian blue (PB) composite to obtain a second mixture, thoroughly stirring the second mixture, and drying a resulting system at room temperature to obtain the hemostatic, antibacterial, and healing-promoting clay mineral-based hydrogel, wherein the kaolinite and PB composite comprises nano-kaolinite and PB in-situ growing on the nano-kaolinite;

wherein a method for preparing the kaolinite and PB composite comprises the following steps:

adding potassium ferricyanide and polyvinylpyrrolidone (PVP) to dilute hydrochloric acid, and subjecting a resulting mixture to stirring and an ultrasonic treatment at a room temperature to obtain a homogeneous solution; and adding the nano-kaolinite to the homogeneous solution to obtain a mixed solution, subjecting the mixed solution to an ultrasonic treatment and thorough stirring, and allowing a resulting system to stand to obtain the blue kaolinite and PB composite.

2. The method according to claim 1, wherein the nano-kaolinite is obtained through intercalation and stripping of pharmaceutical-grade kaolinite.

3. The method according to claim 1, wherein a concentration of the kaolinite and PB composite in the chitosan solution is 0.5 mg/mL to 2 mg/mL.

4. The method according to claim 1, wherein a method for preparing the nano-kaolinite comprises:

subjecting kaolinite to intercalation with dimethyl sulfoxide (DMSO) and urea successively, subjecting a resulting system to an ultrasonic treatment and centrifugation, and washing a resulting precipitate to obtain the nano-kaolinite.

5. The method according to claim 1, wherein a mass percentage of the PB in the kaolinite and PB composite is 10% to 50%.

6. The method according to claim 1, wherein the kaolinite and PB composite has a particle size of 200 nm to 500 nm.

7. The method according to claim 1, wherein a mass percentage of the chitosan in the chitosan solution is 1% to 5%; a volume percentage of the dilute acid is 0.5% to 2%, and the dilute acid is one selected from a group consisting of an acetic acid and a hydrochloric acid; a mass of the crosslinking agent is 10% to 20% of a mass of the chitosan solution; the crosslinking agent is one or a combination of two or more selected from the group consisting of gelatin, glycerin, pectin, and polyvinyl alcohol (PVA); and a viscosity of the chitosan solution is at least 400 Mpa·s.

8. The method according to claim 1, wherein the resulting system is allowed to stand for 15 h to 24 h in an oil/water bath at 60° C. to 90° C.; a mass ratio of the nano-kaolinite to the potassium ferricyanide is 1:3 to 4:3; and a mass ratio of the nano-kaolinite to the PVP is 1:60 to 4:60.

9. A hemostatic, antibacterial, and healing-promoting clay mineral-based hydrogel prepared by the method according to claim 1.

* * * * *